United States Patent
Marczyk (10) Patent No.: US 9,808,317 B2
(45) Date of Patent: Nov. 7, 2017

(54) PNEUMATIC SYSTEM FOR DEPLOYMENT OF ARTICULATING ARMS FOR AN ACCESS PORT

(71) Applicant: Covidien LP, Mansfield, MA (US)

(72) Inventor: Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 575 days.

(21) Appl. No.: 13/735,068

(22) Filed: Jan. 7, 2013

(65) Prior Publication Data

US 2013/0178869 A1   Jul. 11, 2013

Related U.S. Application Data (60) Provisional application No. 61/584,738, filed on Jan. 9, 2012.

(51) Int. Cl.
| | | |
|---|---|---|
| *A61B 17/00* | (2006.01) | |
| *A61B 19/00* | (2006.01) | |
| *A61B 90/10* | (2016.01) | |
| *A61B 17/29* | (2006.01) | |
| *A61B 17/34* | (2006.01) | |

(52) U.S. Cl.
CPC .......... *A61B 19/20* (2013.01); *A61B 17/3423* (2013.01); *A61B 90/10* (2016.02); *A61B 17/3421* (2013.01); *A61B 2017/003* (2013.01); *A61B 2017/2901* (2013.01); *A61B 2017/2902* (2013.01); *A61B 2017/2903* (2013.01); *A61B 2017/2904* (2013.01); *A61B 2017/2905* (2013.01); *A61B 2017/2906* (2013.01); *A61B 2017/2908* (2013.01); *A61B 2017/3447* (2013.01); *A61B 2017/3466* (2013.01)

(58) Field of Classification Search
CPC ................ A61B 19/22; A61B 19/2203; A61B 2019/2242; A61B 2017/2901–2017/2908
USPC .............. 606/1, 130, 151, 198; 604/104–109
See application file for complete search history.

(56) References Cited

U.S. PATENT DOCUMENTS

| | | | |
|---|---|---|---|
| 4,998,916 A | 3/1991 | Hammerslag et al. | |
| 5,441,483 A | 8/1995 | Avitall | |
| 6,231,561 B1 * | 5/2001 | Frazier ............ | A61B 17/00234 604/500 |
| 6,352,503 B1 * | 3/2002 | Matsui et al. ................ | 600/104 |
| 7,044,134 B2 * | 5/2006 | Khairkhahan et al. ....... | 128/887 |
| 7,250,027 B2 | 7/2007 | Barry | |
| 7,608,056 B2 | 10/2009 | Kennedy, II | |
| 7,637,903 B2 | 12/2009 | Lentz et al. | |
| 7,682,319 B2 | 3/2010 | Martin et al. | |
| 7,850,600 B1 * | 12/2010 | Piskun ......................... | 600/114 |
| 2002/0045915 A1 | 4/2002 | Balceta et al. | |
| 2005/0065397 A1 * | 3/2005 | Saadat et al. ................ | 600/104 |
| 2005/0192599 A1 * | 9/2005 | Demarais .......... | A61B 17/0057 606/151 |
| 2006/0235368 A1 * | 10/2006 | Oz ................................... | 606/1 |

(Continued)

*Primary Examiner* — Lynsey Eiseman
*Assistant Examiner* — Sebastian X Lukjan (57) ABSTRACT

A surgical apparatus for positioning within a tissue tract accessing an underlying body cavity is adapted to articulate instruments inserted therein. The surgical apparatus includes an anchor member configured to form a sealing relation with a tissue, a balloon member and a plurality of articulating arms extending distally from the anchor member. Inflating and/or deflating the balloon member effectuate articulation of the articulating arms.

20 Claims, 8 Drawing Sheets

(56) References Cited

U.S. PATENT DOCUMENTS

| | | | |
|---|---|---|---|
| 2007/0032702 A1* | 2/2007 | Ortiz | A61B 17/0218 600/205 |
| 2007/0270679 A1 | 11/2007 | Nguyen et al. | |
| 2009/0043299 A1 | 2/2009 | Racz | |
| 2010/0041945 A1* | 2/2010 | Isbell, Jr. | A61B 17/29 600/104 |
| 2012/0095498 A1* | 4/2012 | Stefanchik | A61B 17/0218 606/198 |
| 2012/0253327 A1* | 10/2012 | Malkowski | 606/1 |

* cited by examiner

PNEUMATIC SYSTEM FOR DEPLOYMENT OF ARTICULATING ARMS FOR AN ACCESS PORT

CROSS-REFERENCE TO RELATED APPLICATIONS

This application claims the benefit of and priority to U.S. Provisional Patent Application No. 61/584,738, filed Jan. 9, 2012, the entire disclosure of which is incorporated by reference herein.

BACKGROUND

1. Technical Field

The present disclosure relates generally to surgical instruments for use with a seal anchor member. More particularly, the present disclosure relates to articulating surgical instruments usable with a seal anchor member that provides multiple instrument access through a single incision in a minimally invasive surgical procedure.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

During procedures employing multiple surgical instruments through a single incision access device, it is advantageous to coordinate the positioning of the end effectors of each surgical instrument. In situations where one or more of the surgical instruments is an articulating surgical instrument, manipulating the articulating surgical instrument or instruments to coordinate the positions of the end effectors is desirable.

Typically, in the prior art, mechanisms that enable articulation of the surgical instruments employ links, screws, cams or cable systems with drawbacks such as difficult placement and cumbersome use.

Hence, a continuing need exists for coordinating the end effectors of articulating surgical instruments used with an access device that permits multiple instruments to be used through a single incision.

SUMMARY

Disclosed herein is a surgical apparatus for positioning within a tissue tract accessing an underlying body cavity. The surgical apparatus includes an anchor member defining a longitudinal axis, a proximal end and a distal end; a balloon member extending distally from the distal end of the anchor member; and an articulating arm extending distally from the distal end of the anchor member, and defining one longitudinal lumen to receive a surgical instrument therethrough.

The articulating arm defines a linear position and an articulated position. The articulating arm transitions between the linear position and the articulated position during inflation and/or deflation of the balloon member. The balloon member is configured to expand in a radial dimension upon inflation.

The articulating arm includes a flexible cable disposed within the articulating arm. Additionally, the articulating arm includes at least one rigid member and at least one flexible member, and the flexible member defines a gooseneck or accordion configuration.

In one embodiment, the articulating arm includes three rigid members and two flexible members, each flexible member intermittently disposed between each pair of adjacent rigid members. The two flexible members include a proximal flexible member defining a first rotational limit, and a distal flexible member defining a second rotational limit. The second rotational limit is greater than the first rotational limit.

The surgical apparatus may include a plurality of articulating arms circumferentially arranged with respect to the balloon member.

The surgical apparatus may also include an inflation system to inflate and deflate the balloon member. In some embodiments, the inflation system includes a piston therein configured to move in a proximal direction, and the proximal movement of the piston articulates the articulating arm.

Also disclosed is a method of articulating a surgical instrument positioned within a tissue tract accessing an underlying body cavity. The method includes positioning a surgical apparatus within the tissue tract. The surgical apparatus includes an anchor member defining a longitudinal axis, a proximal end and a distal end; a balloon member extending distally from the distal end of the anchor member; and an articulating arm extending distally from the distal end of the anchor member. The method further includes inserting the surgical instrument into the articulating arm, and introducing an inflation medium to the balloon member to articulate the articulating arm.

The method may also include introducing the inflation medium to the balloon member to expand the balloon member in a radial dimension. The same process may also transition the articulating arm from a linear configuration to an articulated configuration. By analogy, the reverse process, i.e., withdrawing the inflation medium from the balloon member, transitions the articulating arm from the articulated configuration to the linear configuration.

The surgical apparatus used in the method may include a piston configured to articulate the articulating arm. Introducing the inflation medium drives the piston in a proximal movement to articulate the articulating arm.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

The present disclosure describes a surgical apparatus and methods of deploying articulating arms of a surgical apparatus into a triangulated position with the use of a fluid system such as a pneumatic or hydraulic balloon.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein employs a device that facilitates multiple instrument access through a single incision. This is a minimally invasive surgical procedure, which permits a user to operate through a single entry point, typically the patient's navel. Additionally, the presently disclosed device may be used in a procedure where a naturally occurring orifice (e.g. vagina or anus) is the point of entry to the surgical site. The disclosed procedure involves insufflating the body cavity and positioning a portal member within, e.g., the navel of the patient. Instruments including an endoscope and additional instruments such as graspers, staplers, forceps or the like may be introduced within a portal member to carry out the surgical procedure. An example of such a surgical portal is disclosed in U.S. patent application Ser. No. 12/244,024, Pub. No. US 2009/0093752 A1, filed Oct. 2, 2008, the entire contents of which are hereby incorporated by reference herein.

Figure 1:
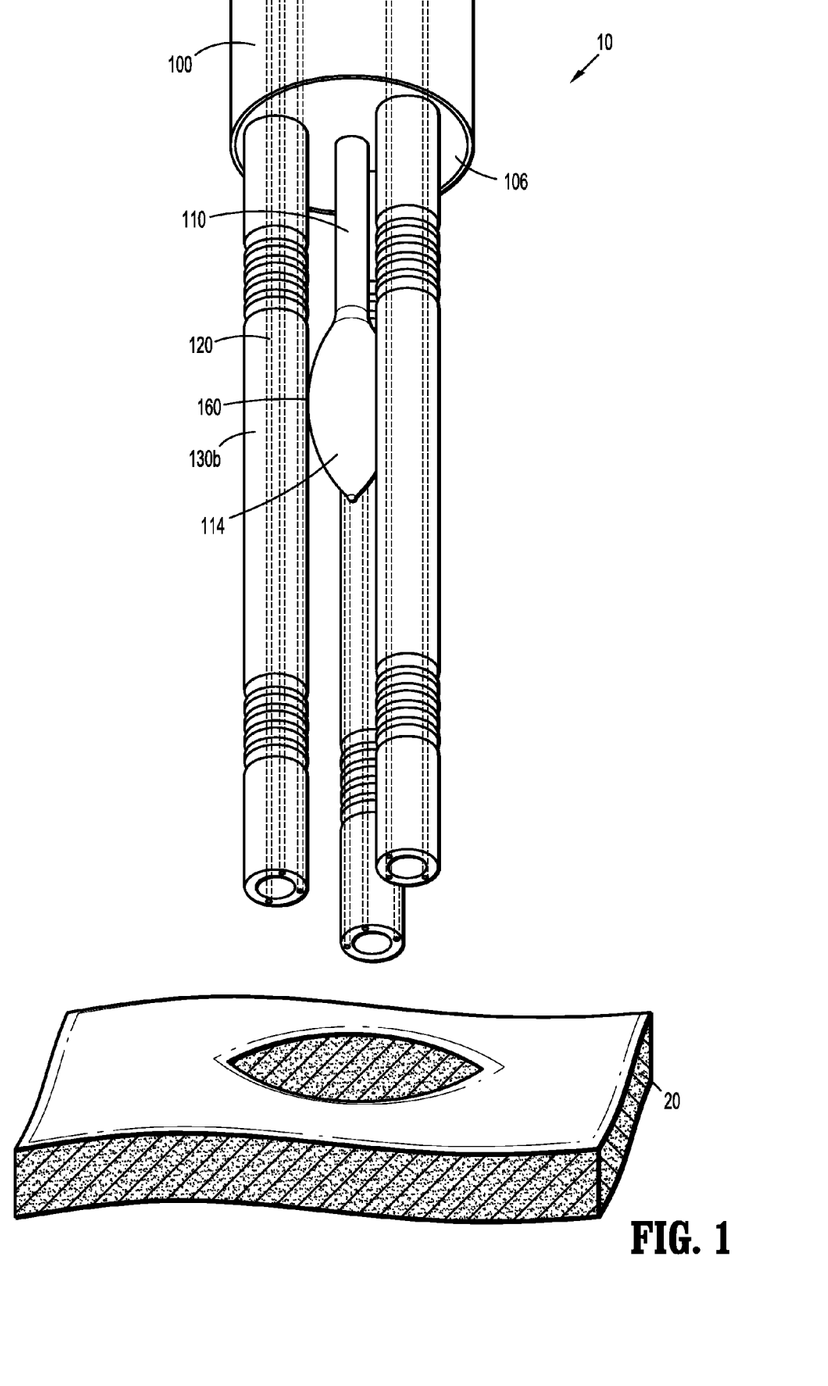
FIG. 1 is a front perspective view of a surgical apparatus in accordance with the principles of the present disclosure illustrating an anchor member with articulating arms positioned relative to a tissue.

Referring now to the drawings, in which like reference numerals identify identical or substantially similar parts throughout the several views, FIG. 1 illustrates a surgical apparatus 10 adapted for insertion within a tissue tract 20, e.g., through the abdominal or peritoneal lining in connection with a laparoscopic surgical procedure. The surgical apparatus 10 has an anchor member 100 for securing the surgical apparatus 10 with respect to the tissue tract 20. The surgical apparatus 10 further includes a balloon member 110 and at least one articulating arm 120 distally connected to the anchor member 100.

Figure 2:
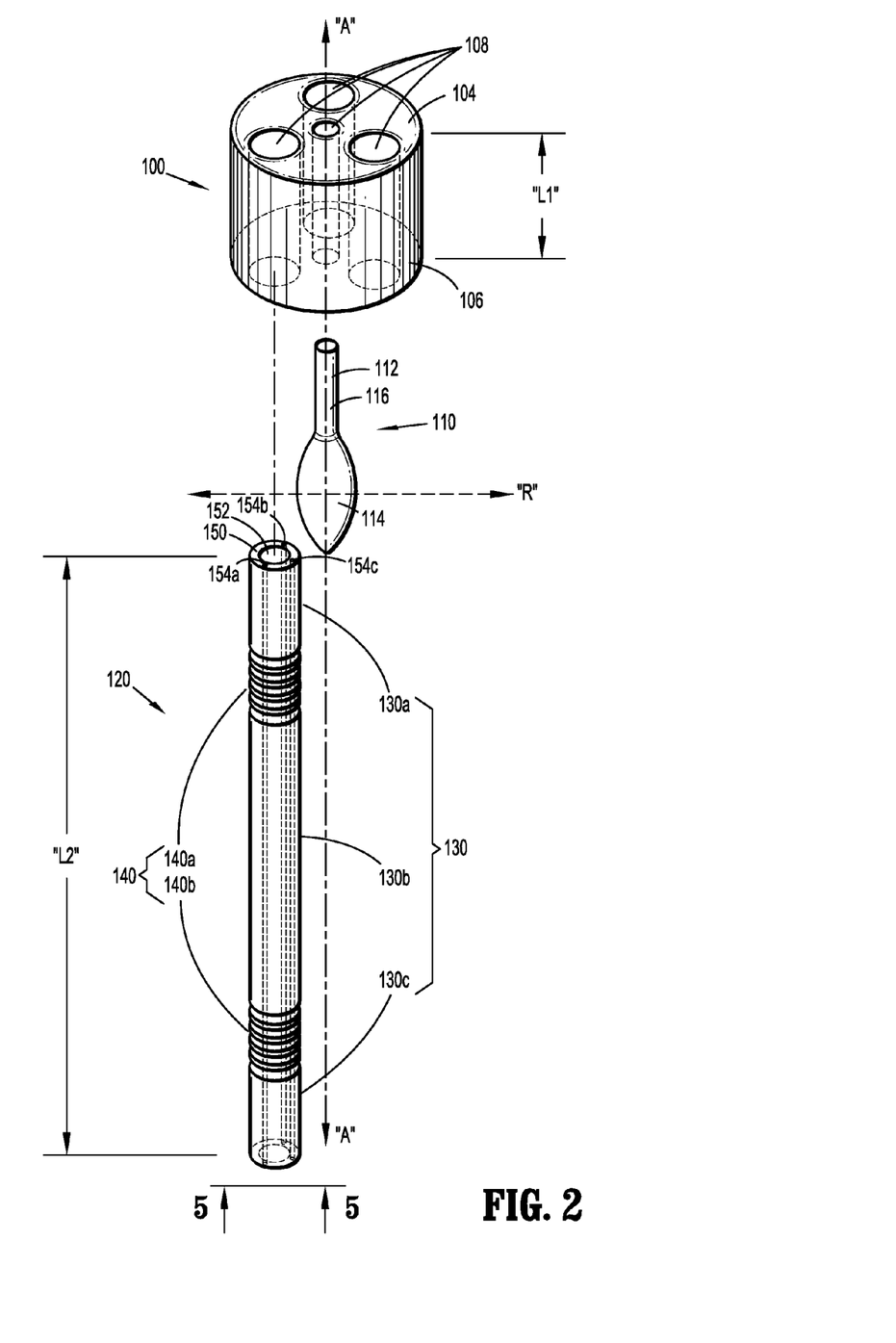
FIG. 2 is an exploded view of the surgical apparatus of FIG. 1.

FIG. 2 is an exploded view of the surgical apparatus 10. For clarity purposes, only one articulating arm 120 is shown. As illustrated in FIG. 2, the anchor member 100 defines a central longitudinal axis "A," a proximal end 104, a distal end 106, and defines at least one longitudinal passage 108 extending between the proximal end 104 and the distal end 106.

The anchor member 100 may include a plurality of longitudinal passages 108, such as four longitudinal passages 108 shown in FIG. 2. The longitudinal passages 108 may have uniform dimensions or different dimensions. It is envisioned that at least one longitudinal passage 108 is dimensioned to receive the balloon member 110. It is also envisioned that at least one longitudinal passage 108 is dimensioned to receive the articulating arm 120.

The anchor member 100 has a longitudinal length "L1," greater than or equal to the minimum length required to anchor the surgical apparatus 10 within any type of tissue tract 20. The anchor member 100 may define a generally cylindrical configuration. However, it is contemplated that the anchor member 100 may define other configurations both prior and subsequent to insertion within the tissue tract 20.

The anchor member 100 may be made from a semi-resilient, disposable, compressible, and flexible type material, for example, but not limited to, a suitable foam, gel material, or soft rubber having sufficient compliance to establish a sealing relation with the tissue tract 20. In one embodiment, the foam includes a polyisoprene material.

Figure 3:
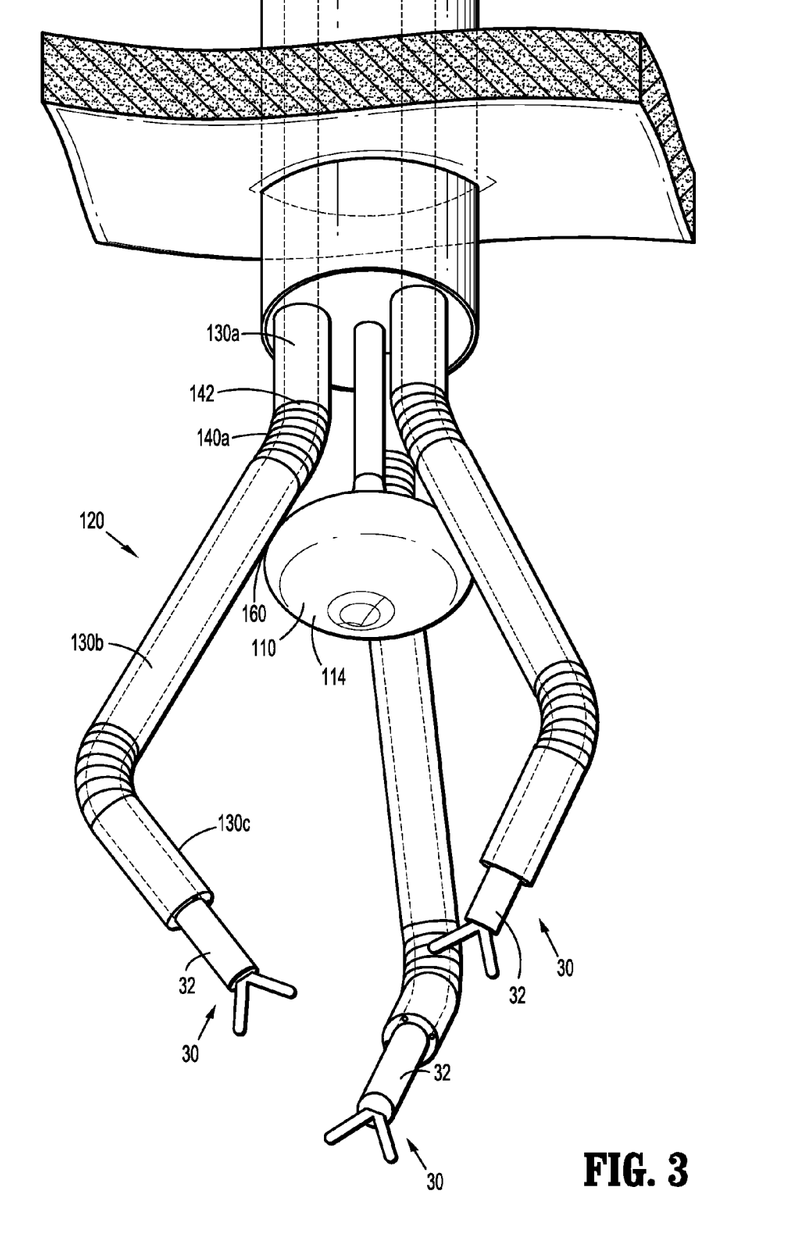
FIG. 3 is a front perspective view of the anchor member with articulating arms of FIG. 1 in an articulated position.

As shown in FIG. 2, the balloon member 110 extends distally from the distal end 106 of the anchor member 100. The balloon member 110 defines a deflated state as illustrated in FIG. 2 and an inflated state as illustrated in FIG. 3. In one embodiment, the balloon member 110 is coaxially aligned with respect to the central longitudinal axis "A," as shown in FIG. 2. In an alternate embodiment, the balloon member 110 may be positioned off the central longitudinal axis "A."

The balloon member 110 may have a composite construction. Specifically, the balloon member 110 may have a first member 112 and a second member 114. The first member 112 exhibits a generally cylindrical configuration elongated along the central longitudinal axis "A." The second member 114 exhibits a generally ovoid or bladder configuration. It is also envisioned that the first and second members 112, 114 may exhibit other configurations.

In one embodiment, the second member 114 is made of an inflatable, elastic material and configured to expand in a radial dimension "R" upon inflation. The first member 112, on the other hand, is made of a relatively rigid material and maintains the same physical dimension during inflation. In an alternate embodiment, the second member 114 is configured to expand in the longitudinal dimension "A," or configured to expand in both the longitudinal dimension "A" and the radial dimension "R" upon inflation. In another alternate embodiment, the first member 112 is also made of an inflatable, elastic material, and configured to expand in either the longitudinal dimension "A" or the radial dimension "R", or both dimensions, upon inflation.

The first member 112 of the balloon member 110 defines a channel 116 therein. In one embodiment, the channel 116 is coupled to an inflation system 40, illustrated in FIGS. 4A-B, to deliver an inflation medium to the second member 114. Details regarding the inflation system 40 are described later.

In one embodiment, the balloon member 110 may expand radially only to a specific maximum volume. Additional inflation pressure will not increase the volume of the balloon member 110. To achieve the above effect, the balloon member 110 may be used in conjunction with a net, such that the net envelops the balloon member 110 to prevent expansion of the balloon member 110 once the balloon member 110 reaches the specific maximum volume.

The balloon member 110 is connected to the anchor member 100. In one embodiment, a portion of the first member 112 of the balloon member 110 is disposed within a longitudinal passage 108 of the anchor member 110, and the remaining portion of the first member 112 together with the second member 114 are disposed distally with respect to the longitudinal passage 108. The first member 112 may be releasably connected to the longitudinal passage 108 via frictional engagement, and the first member 112 can be repositioned along the longitudinal passage 108 until a desired position has been reached. When the first member 112 frictionally engages the longitudinal passage 108, a substantial sealing relation is established therebetween. The first member 112 may also be permanently attached to the longitudinal passage 108 via adhesives, welding or by an overmolding process.

In an alternate embodiment, the balloon member 110 is distally attached to the distal end 106 of the anchor member 100. Specifically, a proximal end of the first member 112 abuts the distal end 106 of the anchor member 100. The first member 112 is coaxially aligned with respect a longitudinal passage 108. The longitudinal passage 108 is operatively connected to the inflation system 40. The longitudinal passage 108 and the channel 116 defined by the first member 112 together define a continuous longitudinal passage to deliver inflation medium from the inflation system 40 to the second member 114. The balloon member 110 may be permanently attached to the distal end 106 of the anchor member 100 by adhesives, welding, or by an overmolding process.

The surgical apparatus 10 further includes at least one articulating arm 120 extending distally from the anchor member 100. The articulating arm 120 defines a linear configuration, as illustrated in FIG. 2, in which the articulating arm 120 is generally aligned along a longitudinal axis parallel to the central longitudinal axis "A." In its linear configuration, the articulating arm 120 defines a longitudinal length "L2." In one embodiment, the longitudinal length "L2" of the articulating arm 120 is substantially larger than the longitudinal length "L1" of the anchor member 100. The articulating arm 120 also defines an articulated configuration, as shown in FIG. 3, in which the articulating arm 120 is curled or clenched.

The articulating arm 120 includes at least one rigid member 130 and at least one flexible member 140. The articulating arm 120 may include a plurality of rigid members 130 and a plurality of flexible members 140 intermittently disposed among the plurality of rigid members 130. In one embodiment as shown in FIG. 2, the articulating arm 120 includes three axially disposed rigid members 130: a proximal rigid member 130a, a middle rigid member 130b and a distal rigid member 130c. Each rigid member 130 exhibits a generally cylindrical configuration. The articulating arm 120 further includes two flexible members 140: a proximal flexible member 140a and a distal flexible member 140b, which are intermittently disposed between each pair of adjacent rigid members 130. Each flexible member 140 has a gooseneck or accordion-like configuration. In FIG. 2, the rigid members 130 and the flexible members 140 are arranged from the proximal end to the distal end of the articulating arm 102 in the following order: the proximal rigid member 130a, the proximal flexible member 140a, the middle rigid member 130b, the distal flexible member 140b, and the distal rigid member 130c.

The rigid members 130 and the flexible members 140 together form a circular wall 150 extending along the length "L2" of the articulating arm 120. The circular wall 150 defines a longitudinal lumen 152 at the center thereof. The longitudinal lumen 152 also has a length of "L2." The longitudinal lumen 152 is dimensioned to receive a surgical instrument 30 as shown in FIG. 3. The surgical instrument 30 could be any surgical instrument such as grasper, stapler, forceps or the like.

The circular wall 150 further defines at least one channel, e.g. 154a, 154b, or 154c, of a length "L2" positioned circumferentially about the longitudinal lumen 152. The circular wall 150 may define a plurality of channels, e.g. 154a-c, therein. In one embodiment as illustrated in FIG. 2, the circular wall 150 defines three channels 154a-c. The channels 154a-c may be symmetrically disposed. Alternately, as shown in FIG. 5, which is a cross-sectional view of the articulating arm 120, two of the channels 154a-b are disposed on an x-axis, and the third channel 154c is disposed on a y-axis. Each of the channels 154a-c is dimensioned to receive a flexible cable or wire therein. The flexible cable is used to facilitate stabilization and articulation of the articulating arm 120.

The articulating arm 120 may be connected to the anchor member 100 in a manner similar to the way the balloon member 110 connected to the anchor member 100. In one embodiment, a portion of the articulating arm 120 is disposed within a longitudinal passage 108 of the anchor member 100, and the remaining portion of the articulating arm 120 extends distally beyond the longitudinal passage 108. The articulating arm 120 may be releasably connected to the longitudinal passage 108 via frictional engagement, and the articulating arm 120 can be repositioned along the longitudinal passage 108 until a desired position has reached. When the articulating arm 120 frictionally engages the longitudinal passage 108, a substantial sealing relation is established therebetween. The articulating arm 120 may also be permanently attached to the longitudinal passage 108 via adhesives or other similar mechanisms.

The articulating arm 120 is positioned relative to the balloon member 110 in a manner such that inflation and deflation of the balloon member 110 would transition the articulating arm 120 between its linear configuration and its articulated configuration. In one embodiment, as shown in FIG. 1, the middle rigid member 130b and the second member 114 of the balloon member 110 are disposed distally with respect to the distal end 106 to the same extent.

It is envisioned that the articulating arm 120 remains in contact with the balloon member 110 during inflation and deflation. In FIG. 1, the articulating arm 120 contacts the deflated balloon member 110 at one contact point 160, which is the same point where the second member 114 of the balloon member 110 meets the middle rigid member 130b of the articulating arm 120. The contact point 160 may be anywhere along the length of the middle rigid member 130b and anywhere along the length of the second member 114. In one embodiment as in FIG. 1, the contact point 160 is about one third way down the length of the middle rigid member 130b, and about half way down the longitudinal length of the second member 114.

Figure 1A:
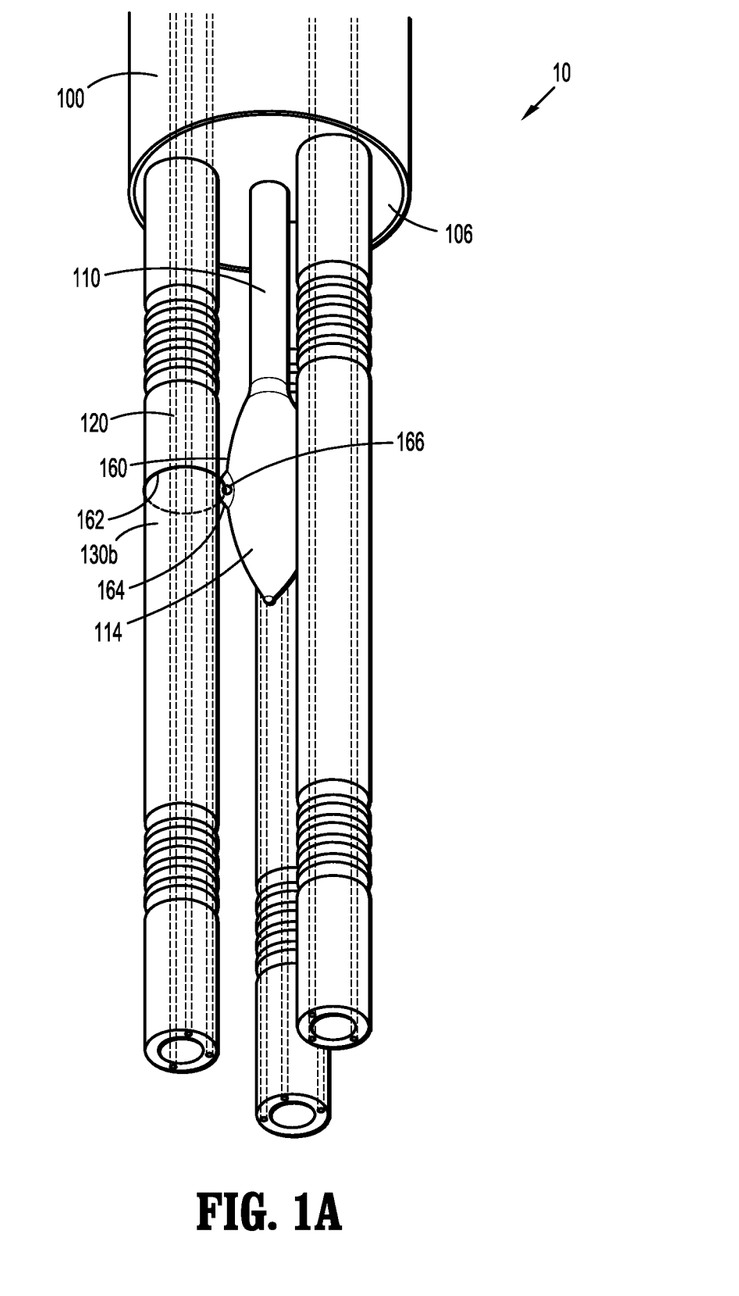
FIG. 1A a front perspective view of an alternate embodiment of the surgical apparatus of FIG. 1.

In another embodiment, as illustrated in FIG. 1A, the second member 114 may be securely attached to the middle rigid member 130b at the contact point 160 via a hoop 162. The hoop 162 circumferentially surrounds the middle rigid member 130. The second member 114 includes a protrusion 164 defining an opening 166 which allows the hoop 162 to travel therethrough.

Figures 6A, 6B:
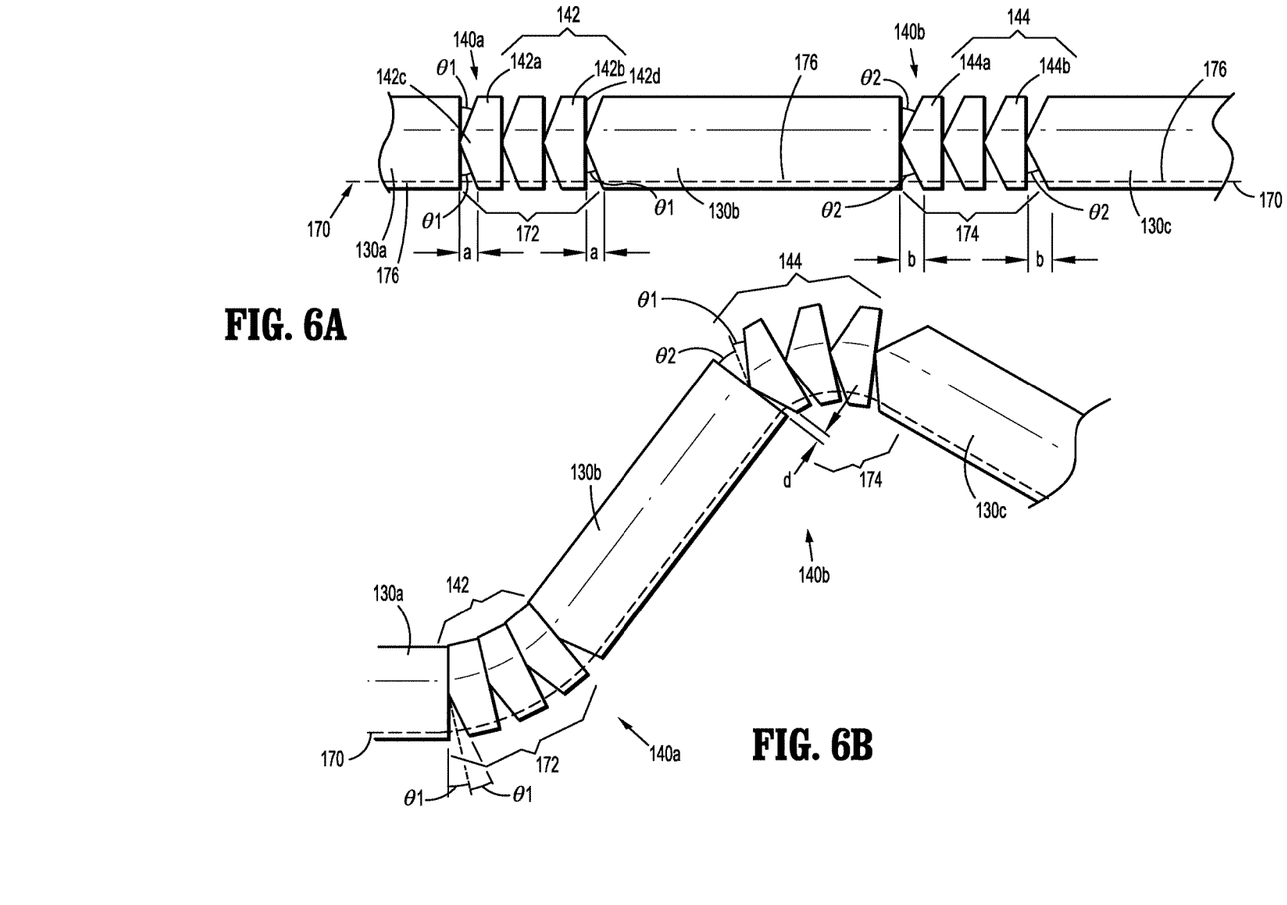
FIG. 6A is a schematic view of one articulating arm in a linear position.
FIG. 6B is a schematic view of the articulating arm of FIG. 6A in a first, partially articulated position.
Figure 6C:
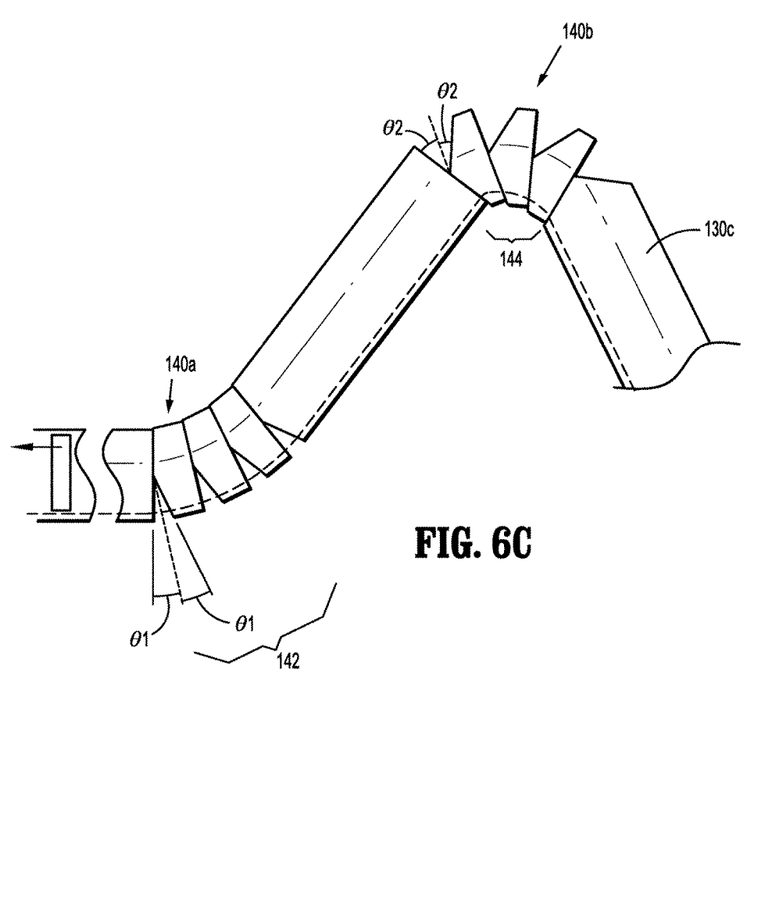
FIG. 6C is a schematic view of the articulating arm of FIG. 6A in a second, fully articulated position.

Details regarding articulation of a single articulating arm 120 are illustrated in FIGS. 6A-C. As illustrated in FIG. 6A, the proximal flexible member 140a includes a plurality of proximal links 142, including a first proximal link 142a connected to the proximal rigid member 130a, and a last proximal link 142b connected to the middle rigid member 130b. Similarly, the distal flexible member 140b includes a plurality of distal links 144, including a first distal link 144a connected to the middle rigid member 130b, and a last distal link 144b connected to the distal rigid member 130c.

In one embodiment, as illustrated in FIG. 6A, each proximal link 142 defines a conical proximal end 142c and a flat distal end 142d. When the proximal links 142 are arranged in a linear configuration, each proximal link 142 has a rotational limit of $\theta 1$ in both clockwise and counterclockwise directions. Further, the rotational limit $\theta 1$ corresponds to a gap "a" between adjacent proximal links 142. Similarly, the middle rigid member 130b also has a rotational limit of $\theta 1$ in both clockwise and counterclockwise directions from its linear position, and has a gap "a" with respect to the last proximal link 142b.

The distal links 144 are arranged in a similar fashion as the proximal links 142, except that the each distal link 144 has a rotational limit $\theta 2$ corresponding to a gap "b." The rotational limit $\theta 2$ is greater than the rotational limit $\theta 1$. For that reason, the gap "b" is also larger than the gap "a." Likewise, the distal rigid member 130c also defines a rotational limit $\theta 2$, and has a gap "b" with respect to the last distal link 144b.

Due to the above configuration, the middle rigid member 130b can be pivoted with respect to the proximal rigid member 130a about the proximal flexible member 140a, and simultaneously varying the gap "a" defined in the proximal links 142. Similarly, the distal rigid member 130c can be pivoted with respect to the middle rigid member 130b about the distal flexible member 140b, and simultaneously varying the gap "b" defined in the distal links 144.

Additionally, as illustrated in FIG. 6A, each articulating arm 120 includes at least one cable 170 running through one of the small channels 154a-c defined in the circumference of the articulating arm 120. For clarity purposes, FIG. 6A only shows one cable 170 without showing the small channels 154a-c. The cable 170 has a flexible nature allowing it to be easily conformed to the configuration of the articulating arm 120.

The cable 170 defines a constant length, and includes a first portion 172 passing through the proximal flexible member 140a, and a second portion 174 passing through the distal flexible member 140b, and a remaining portion 176 that is disposed in the rigid members 130a-c. Since the rigid members 130a-c have a relatively constant dimension compared to the flexible members 140a-b, the length of the remaining portion 176 of the cable 170 that is disposed in the rigid members 130a-c remains constant.

Accordingly, a change in length of the first portion 172 is compensated by a change in length of the second portion 174, and vice versa. For instance, an increase in gap "a" in the proximal flexible member 140a results an increase in length of the first portion 172 of the cable 170, which inevitably demands a decrease in length of the second portion 174 of the cable 170. Reduction in length of the second portion 174 causes a decrease in gap "b" in the distal flexible member 140b. For these reasons, as shown in FIG. 6B, any pivotal motion of the middle rigid member 130b in a counterclockwise direction with respect to the proximal rigid member 130a that increases the gap "a" in the proximal flexible member 140a would inevitably require pivotal motion of the distal rigid member 130c in a clockwise direction with respect to the middle rigid member 130c to decrease the gap "b" in the distal flexible member 140b.

With reference to FIG. 3, during inflation of the balloon member 110, the second member 114 of the balloon member 110 expands radially outwardly and pushes the middle rigid member 130b of the articulating arm 120 outwardly via the contact point 160. As a result of the inflation, the articulating arm 120 exhibits a curled or claw configuration. More specifically, the middle rigid member 130b pivots with respect to the proximal rigid member 130a about the proximal flexible member 140a until the proximal links 142 in the proximal flexible member 140a reach their rotational limit $\theta 1$. During this process, the distal rigid member 130c would also pivot inwardly.

Similarly, deflation of the balloon member 110 would cause reverse behavior of the articulating arm 120, and resumes the articulating arm 120 from its articulated position shown in FIG. 3 to its linear configuration as shown in FIG. 1. In one embodiment, the cable 170 has a resilient material with a resilient nature that tends to resume its original linear configuration in the absence of any biasing force. The biasing force could be the force applied by the balloon member 110 which increases as the balloon member 110 inflates and decreases as the balloon member 110 deflates. In an alternate embodiment, the articulating arm 120 includes other spring mechanisms, parallel to the cable 170, that tends to resume the articulating arm 120 to its linear configuration as the balloon member 110 deflates.

In one embodiment, when the balloon member 110 reaches its maximally inflated state, the proximal links 142 in the proximal flexible member 140a would have also reached their rotational limit $\theta 1$, as illustrated in FIG. 6B. When each proximal link 142 reaches its rotational limit $\theta 1$, each distal link 144 would pivot for an extent less than its rotational limit $\theta 2$. For instance, adjacent distal links 144 in the distal flexible member 140b still have a gap "d" defined therebetween. It is envisioned that the distal flexible member 140b may be further rotated to reach their rotational limit $\theta 2$ by pulling the cable 170 in a proximal direction.

Figure 4A:
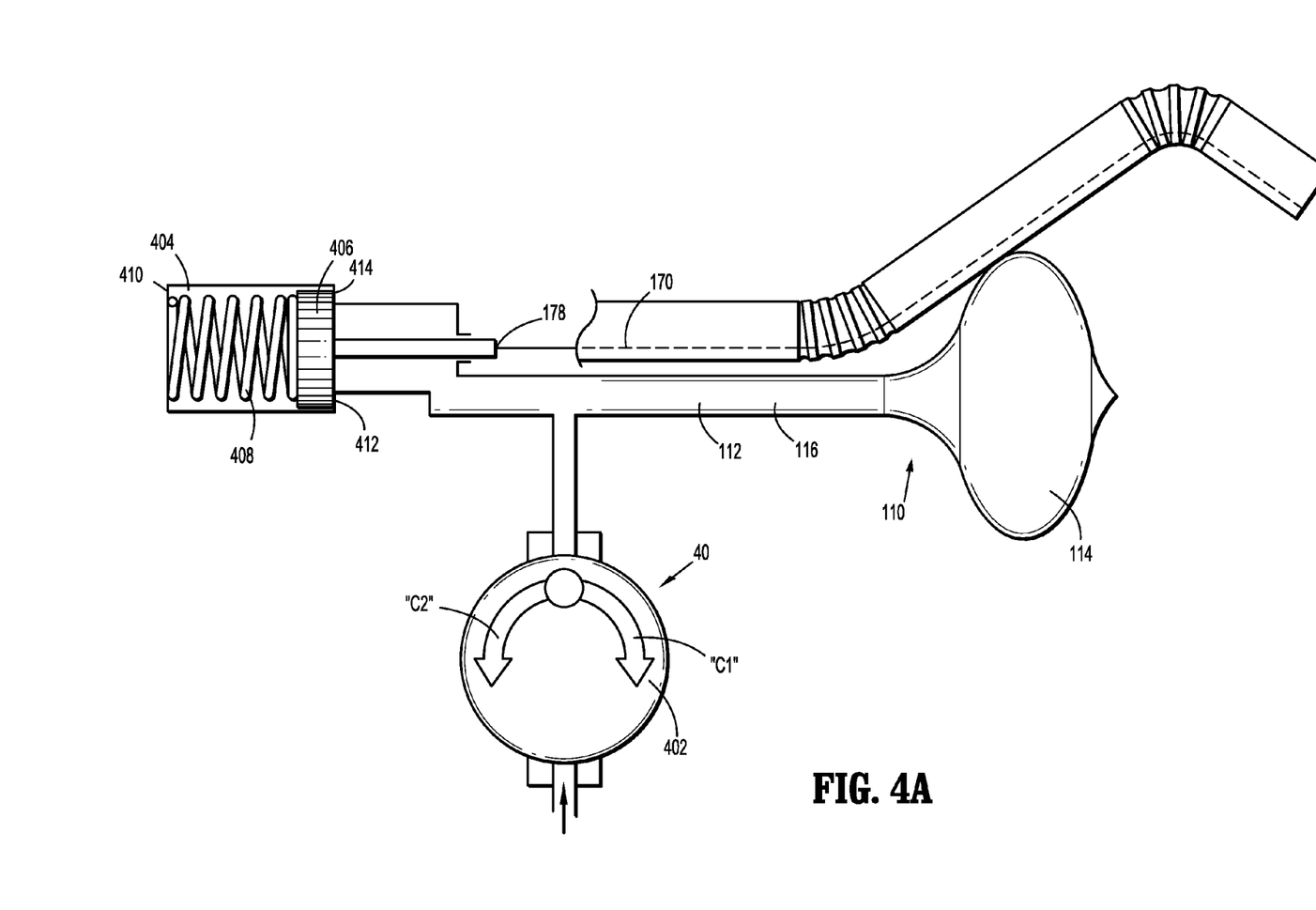
FIGS. 4A-4B are schematic views of an inflation system in connection with the surgical apparatus of FIG. 1.
Figures 4B, 5:
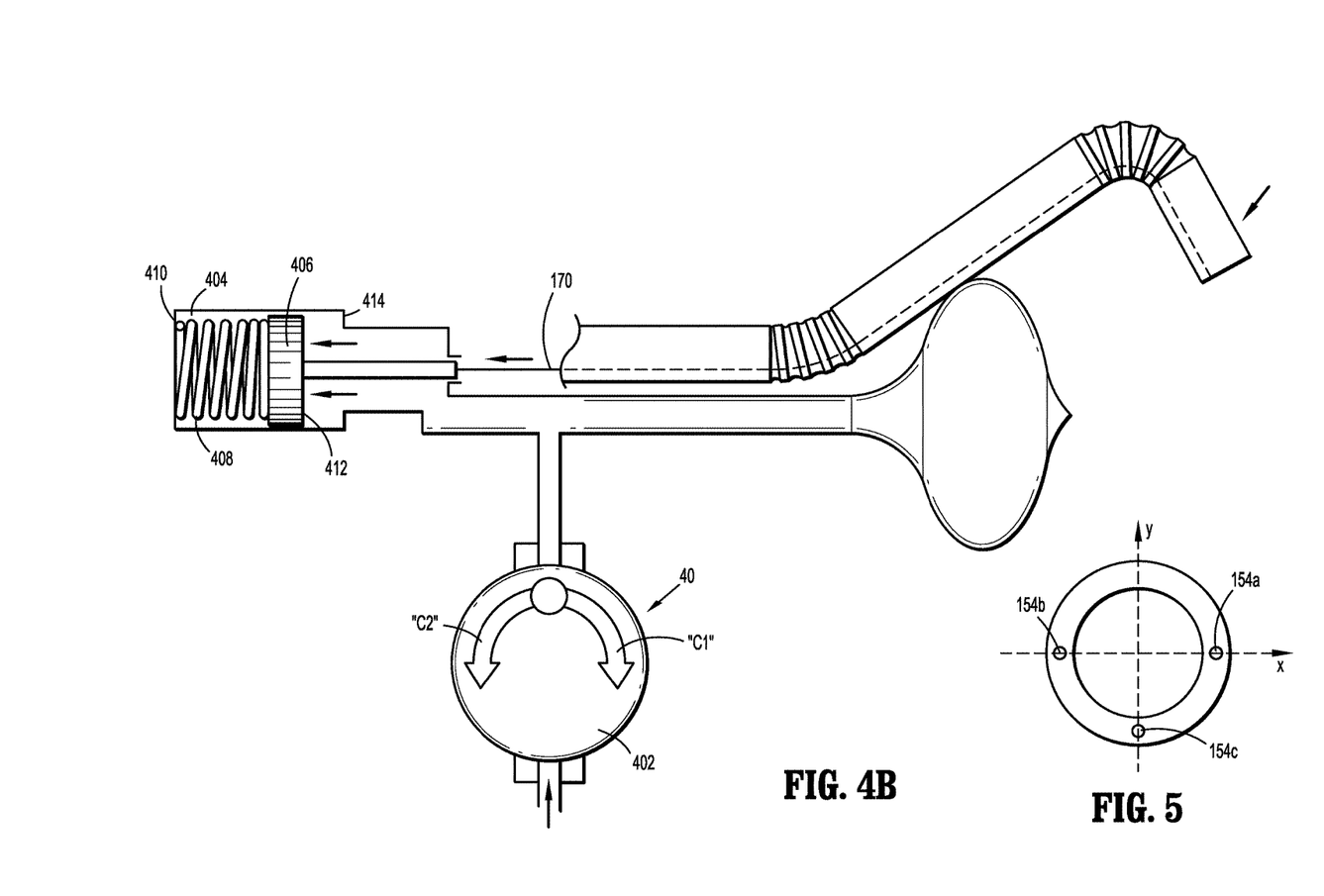
FIG. 5 is a cross-section view of an articulating arm of the surgical apparatus of FIG. 2 taken along the line "5-5" of FIG. 2.

With reference to FIG. 4A, the inflation system 40 includes a rotatable knob 402 to selectively control the amount of inflation and deflation. For instance, a clockwise rotation "C1" of the knob 402 introduces inflation medium to the balloon member 110 thereby inflating the balloon member 110. A counterclockwise rotation "C2" of the knob 402 withdraws inflation medium from the balloon member 110 thereby deflating the balloon member 110. The inflation system 40 may be a hydraulic system or a pneumatic system.

In a certain embodiment, the inflation system 40 may include mechanisms configured to provide additional articulation to the articulating arm 120 after the balloon member 110 reaches its maximum inflated state. For instance, as illustrated in FIG. 4A, the inflation system 40 may include a cylinder 404 which includes a spring loaded piston 406 therein. The cylinder 404 could be an air cylinder. The cylinder 404 is fluidly coupled to the balloon member 110. A spring 408 is positioned between the piston 406 and the proximal end 410 of the cylinder 404. The spring 408 exerts a distal pressure upon the piston 406 and presses the distal end 412 of the piston 406 against the distal end 414 of the cylinder 404. The proximal end 178 of the cable 170 is securely attached to the distal end 412 of the spring loaded piston 406.

The piston 406 remains still against the distal end 414 of the cylinder 404 until the inflation pressure within the balloon member 110 reaches a certain level that overcomes the spring pressure by the spring 408.

In one embodiment, the balloon member 110 may expand radially due to inflation to a specific maximum volume or a maximum inflated state. When the balloon member 110 reaches its maximum inflated state, additional inflation will continuously increase the inflation pressure within the balloon member 110, but will not increase the volume of the balloon member 110. It is envisioned that once the balloon member 110 reaches its maximum inflated state, any additional inflation pressure within the balloon member 110 will overcome the spring pressure of the spring 408, thus inducing movement of the piston 406. Accordingly, in this embodiment, upon inflation, the inflation medium first inflates the balloon member 110 until the balloon member 110 reaches its maximum inflated state, at which point all the proximal links 142 of the proximal flexible member 140a are locked by their rotational limit θ1 as shown in FIG. 6B. Any further inflation thereafter actuated by continuous rotation of the knob 402 in the clockwise direction "C1," as shown in FIG. 4B, overcomes the spring pressure exerted by the spring 408 and drives the piston 406 in a proximal direction. Proximal movement of the piston 406 simultaneously pulls the cable 170 attached thereto in a proximal direction. Proximal movement of the cable 170 causes the distal links 144 to rotate further until each distal link 144 reaches its rotational limit θ2, as illustrated in FIG. 6C. In FIG. 6C, both the proximal and distal flexible members 140a and 140b reach their rotational limits. The distal rigid member 130c as shown in FIG. 6C has an additional inward articulation compared to that in FIG. 6B.

The surgical apparatus 10 may comprise a plurality of articulating arms 120, such as three or four articulating arms 120. The embodiment illustrated in FIG. 1 shows that the surgical apparatus 10 includes three articulating arms 120. The plurality of articulating arms 120 may be symmetrically and circumferentially arranged about the balloon member 110. For instance, the plurality of articulating arms 120 may be spaced equidistant from the balloon member 110 and spaced equally from one another. Alternately, the distance between each articulating arm 120 and the balloon member 110 may vary. The distance between adjacent articulating arms 120 may also vary.

It is envisioned that inflation of the balloon member 110 causes simultaneous articulation of the plurality of articulating arms 120. If surgical instruments 30 are disposed within each of the articulating arm 120, as illustrated in FIG. 3, inflation of the balloon member 110 triangulates the end effectors 32 of the surgical instruments 30 to focus on a target zone. Continuous inflation causes the surgical instruments 30 to reduce their focus by gradually reducing the dimension of the target zone. For similar reasons, deflation causes the surgical instruments 30 to enlarge their focus by increasing the dimension of the target zone.

In operation, the surgeon first introduces the surgical apparatus 10 into the tissue tract 20 until all the articulating arms 120 are beneath the tissue tract 20. At that point, the anchor member 100 forms a substantial sealing relation with the tissue tract 20. Next, the surgeon introduces surgical instruments 30 into each articulating arm 120. It is also envisioned that the surgical instruments 30 may be inserted into each arm 120 before advancing the surgical apparatus 10 into the tissue tract 20. Then, the surgeon activates the rotatable knob 402 of the inflation system 40 to inflate the balloon member 110. Expansion of the balloon member 110 pivots the middle rigid member 130b of the articulating arm 120 outwardly about the proximal flexible member 140a, which, in turn, causes the distal rigid member 130c to pivot inwardly about the distal flexible member 140b. Once the balloon member 110 reaches its maximum inflated state, any inflation thereafter drives the cable 170 in a proximal direction to effectuate additional articulation of the articulating arm 120. During inflation, the articulating arms 120 clench inwardly, triangulate the end effectors 32 of the surgical instruments 30 to focus on a target zone. The surgeon may continue rotating the knob 402 to articulate the arms 120 until the surgical instruments 30 reduce their focus to a desired dimension.

To reset the articulating arms 120 to their linear configuration, the surgeon simply rotates the knob 402 in a reverse direction to effectuate deflation. As discussed earlier, the cables 170 may comprise a resilient material, which, in turn, assist the articulating arms 120 to resume their original linear configuration during deflation. Alternately, the articulating arm 120 incorporates other spring mechanisms with resilient nature, such as elastic wires placed into the channels 154a-c of FIG. 5.

The surgical apparatus 10 and method of its operation as disclosed herein provides significant benefits to the surgeon during surgical procedures. The surgical apparatus 10 allows the surgeon to triangulate the surgical instruments 30 and fine-tune the articulation of the surgical instruments 30, and enables the surgeon to easily control the amount of triangulation of surgical instruments 30 with a single action, i.e., rotation of the knob 402. As a result, the deployment and triangulation of the surgical instruments 30 is effortless, intuitive, and can be handled by a single hand in a single action.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the surgical procedures. Those skilled in the art will envision other modifications within the scope and spirit of the claims appended hereto.

What is claimed is:

1. A surgical apparatus for positioning within a tissue tract accessing an underlying body cavity, which comprises:
   an anchor member defining a longitudinal axis and having a proximal end and a distal end, the distal end having a distal end surface;
   a balloon member extending distally through the distal end surface of the anchor member;
   the balloon member is configured to inflate and deflate, and an articulating arm extending distally through the distal end surface of the anchor member defining a longitudinal lumen, the articulating arm having a linear position and a fully articulated position, wherein in any articulated position of the articulating arm between the linear position and the fully articulated position the lumen is configured to guide a surgical instrument through the entire lumen, wherein the articulating arm is configured to transition between the linear position and the full articulated position in response to inflation and deflation of the balloon member.

2. The surgical apparatus according to claim 1, wherein the balloon member is configured to expand in a radial dimension upon inflation.

3. The surgical apparatus according to claim 1, wherein the balloon member has a deflated configuration and an inflated configuration, and wherein the articulating arm is configured to transition towards the fully articulated position as the balloon member is inflated towards the inflated configuration.

4. The surgical apparatus according to claim 1, wherein the balloon member has a deflated configuration and inflated configuration, and wherein the articulating arm is biased towards the linear position such that the articulating arm transitions towards the linear position as the balloon member is deflated towards the deflated configuration.

5. The surgical apparatus according to claim 1, wherein the articulating arm includes at least one rigid member and at least one flexible member.

6. The surgical apparatus according to claim 1, wherein the articulating arm includes three rigid members and two flexible members, each flexible member intermittently disposed between a pair of adjacent rigid members.

7. The surgical apparatus according to claim 6, wherein the two flexible members include a proximal flexible member defining a first rotational limit, and a distal flexible member defining a second rotational limit.

8. The surgical apparatus according to claim 7, wherein the second rotational limit is greater than the first rotational limit.

9. The surgical apparatus according to claim 1 further including a plurality of articulating arms circumferentially arranged with respect to the balloon member.

10. The surgical apparatus according to claim 1 including an inflation system to inflate and deflate the balloon member.

11. The surgical apparatus according to claim 10, wherein the inflation system includes a piston therein configured to move in a proximal direction.

12. The surgical apparatus according to claim 11, wherein proximal movement of the piston articulates the articulating arm.

13. The surgical apparatus according to claim 1 including a flexible cable disposed within the articulating arm.

14. A method of articulating a surgical instrument positioned within a tissue tract accessing an underlying body cavity, the method comprising:
    positioning a surgical apparatus within the tissue tract, the surgical apparatus including:
    an anchor member defining a longitudinal axis and having a proximal end and a distal end, the distal end having a distal end surface; a balloon member extending distally through the distal end surface of the anchor member; and
    an articulating arm extending distally through the distal end surface of the anchor member;
    inserting the surgical instrument into the articulating arm;
    inflating the balloon member to articulate the articulating arm; and
    guiding the surgical instrument through the entire articulating arm when the articulating arm is in any articulated position between linear position and a fully articulated position.

15. The method of articulating a surgical instrument according to claim 14 including introducing an inflation medium to the balloon member to transition the articulating arm from a linear configuration towards a fully articulated configuration.

16. The method of articulating a surgical instrument according to claim 14 including withdrawing an inflation medium from the balloon member to transition the articulating arm towards a linear configuration.

17. The method of articulating a surgical instrument according to claim 14 including introducing an inflation medium to the balloon member to expand the balloon member in a radial dimension.

18. The method of articulating a surgical instrument according to claim 14, wherein the surgical apparatus includes a piston configured to articulate the articulating arm.

19. The method of articulating a surgical instrument according to claim 18 including introducing an inflation medium to drive the piston in a proximal movement to articulate the articulating arm.

20. The surgical apparatus according to claim 1, wherein the anchor member defines a first longitudinal passage and a second longitudinal passage, the first and second longitudinal passages extending between the proximal and distal ends of the anchor member parallel to the longitudinal axis, the balloon member releasably connected to the first longitudinal passage and the articulating arm releasably connected to the second longitudinal passage.

* * * * *